US012688935B2

(12) United States Patent
Exner et al.

(10) Patent No.: US 12,688,935 B2
(45) Date of Patent: Jul. 21, 2026

(54) DEVICES AND METHODS FOR CONFIGURING A WEARABLE DEVICE FOR EXERCISE TRACKING

(71) Applicant: Sony Group Corporation, Tokyo (JP)

(72) Inventors: Peter Exner, Malmö (SE); Hannes Bergkvist, Rydeback (SE)

(73) Assignee: Sony Group Corporation, Tokyo (JP)

( * ) Notice: Subject to any disclaimer, the term of this patent is extended or adjusted under 35 U.S.C. 154(b) by 783 days.

(21) Appl. No.: 17/966,953

(22) Filed: Oct. 17, 2022

(65) Prior Publication Data

US 2023/0146489 A1 May 11, 2023

(30) Foreign Application Priority Data

Nov. 8, 2021 (SE) .................................... 2151364-3

(51) Int. Cl.
*G16H 40/67* (2018.01)
*A63B 24/00* (2006.01)
(Continued)

(52) U.S. Cl.
CPC ......... *G16H 40/67* (2018.01); *A63B 24/0062* (2013.01); *G06F 1/163* (2013.01);
(Continued)

(58) Field of Classification Search
CPC .... G16H 40/67; G16H 40/40; A63B 24/0062; A63B 2220/05; A63B 2220/803;
(Continued)

(56) References Cited

U.S. PATENT DOCUMENTS

| | | | |
|---|---|---|---|
| 9,213,803 | B2 | 12/2015 | Rolley |
| 9,292,935 | B2 | 3/2016 | Koduri |

(Continued)

FOREIGN PATENT DOCUMENTS

| | | | |
|---|---|---|---|
| KR | 20160087740 A | 7/2016 | |
| WO | 2010083562 A1 | 7/2010 | |
| WO | WO-2020089382 A1 * | 5/2020 | ............. G16H 20/10 |

OTHER PUBLICATIONS

Vijayan V, Connolly JP, Condell J, McKelvey N, Gardiner P. Review of Wearable Devices and Data Collection Considerations for Connected Health. Sensors (Basel). Aug. 19, 2021;21(16):5589. doi: 10.3390/s21165589. PMID: 34451032; PMCID: PMC8402237. (Year: 2021).*

(Continued)

*Primary Examiner* — Sun M Li
(74) *Attorney, Agent, or Firm* — Tucker Ellis LLP

(57) ABSTRACT

An apparatus for configuring a wearable device for exercise tracking includes a data storage unit for storing sensor data generated by a sensor arrangement in the wearable device based on sensed movement of the wearable device and optical movement data including representations of an individual obtained from an image-based monitoring system; and a processing unit configured to: execute a movement tracker model on the sensor data to determine a first exercise activity and an associated first confidence indicator; execute an optical tracker model on the optical movement data to determine a second exercise activity and an associated second confidence indicator; process the movement tracker model based on the first confidence indicator and the second confidence indicator.

20 Claims, 5 Drawing Sheets

10

1

(51) Int. Cl.

| | | |
|---|---|---|
| *G06F 1/16* | (2006.01) | |
| *G06N 7/01* | (2023.01) | |
| *G06N 20/00* | (2019.01) | |
| *G06V 40/20* | (2022.01) | |
| *G16H 40/40* | (2018.01) | |

(52) U.S. Cl.

CPC .............. *G06N 7/01* (2023.01); *G06N 20/00* (2019.01); *G06V 40/23* (2022.01); *G16H 40/40* (2018.01); *A63B 2220/05* (2013.01); *A63B 2220/803* (2013.01); *A63B 2220/805* (2013.01); *A63B 2220/836* (2013.01); *A63B 2225/50* (2013.01)

(58) Field of Classification Search

CPC ........ A63B 2220/805; A63B 2220/836; A63B 2225/50; A63B 71/06; G06F 1/163; G06F 2218/00; G06F 18/25; G06N 7/01; G06N 20/00; G06V 40/23; G06V 10/82; G06V 20/46; G06V 10/34; G06V 10/764; G06V 10/774

See application file for complete search history.

(56) References Cited

U.S. PATENT DOCUMENTS

| | | | | |
|---|---|---|---|---|
| 11,224,359 | B2 * | 1/2022 | Song | G06N 3/0895 |
| 11,405,594 | B2 * | 8/2022 | Lee | H04W 4/80 |
| 12,020,511 | B1 * | 6/2024 | Denton | A63B 24/0062 |
| 2014/0249393 | A1 * | 9/2014 | Proud | H02J 50/70 600/324 |
| 2014/0330408 | A1 * | 11/2014 | Rolley | G16H 10/60 700/91 |
| 2015/0196804 | A1 * | 7/2015 | Koduri | G06Q 10/0639 482/8 |
| 2017/0061820 | A1 * | 3/2017 | Firoozbakhsh | G06Q 20/10 |
| 2017/0232294 | A1 * | 8/2017 | Kruger | G09B 19/003 434/247 |
| 2020/0085366 | A1 * | 3/2020 | Benson | A61B 5/4566 |
| 2020/0113489 | A1 | 4/2020 | Mariani | |
| 2020/0215410 | A1 | 7/2020 | Li | |
| 2021/0104264 | A1 | 4/2021 | Bose | |
| 2021/0154529 | A1 * | 5/2021 | Barr | G06T 13/40 |
| 2021/0192367 | A1 | 6/2021 | Oztaskent | |
| 2021/0225195 | A1 * | 7/2021 | Shteren | G16H 20/30 |
| 2021/0232855 | A1 * | 7/2021 | Yamamoto | G06N 3/084 |
| 2021/0279554 | A1 * | 9/2021 | Ibtehaz | A61B 5/7278 |
| 2021/0394020 | A1 * | 12/2021 | Killen | A63B 24/0006 |
| 2022/0054081 | A1 * | 2/2022 | Lee | G16H 50/20 |
| 2022/0296966 | A1 * | 9/2022 | Asikainen | G16H 20/30 |

OTHER PUBLICATIONS

Arent I, Schmidt FP, Botsch M, Dürr V. Marker-Less Motion Capture of Insect Locomotion With Deep Neural Networks Pretrained on Synthetic Videos. Front Behav Neurosci. Apr. 22, 2021;15:637806. doi: 10.3389/fnbeh.2021.637806. PMID: 33967713; PMCID: PMC8100444. (Year: 2021).*

Irshad MT, Nisar MA, Gouverneur P, Rapp M, Grzegorzek M. AI Approaches Towards Prechtl's Assessment of General Movements : A Systematic Literature Review. Sensors (Basel). Sep. 17, 2020;20(18):5321. doi: 10.3390/s20185321. PMID: 32957598; PMCID: PMC7570604. (Year: 2020).*

C. Zhu, Q. Cheng and W. Sheng, "Human activity recognition via motion and vision data fusion," 2010 Conference Record of the Forty Fourth Asilomar Conference on Signals, Systems and Computers, Pacific Grove, CA, USA, 2010, pp. 332-336, doi: 10.1109/ACSSC.2010.5757529. (Year: 2010).*

Search Report from corresponding Swedish Application No. 2151364-3, mailed on May 30, 2022, 4 pages.

Chun Zhu et al., "Human Activity Recognition Via Motion and Vision Data Fusion", IEEE, dated Nov. 7-10, 2010, 5 pages.

Ahmad Zeeshan et al: "Human Action Recognition Using Deep Multilevel Multimodal (M/\2) Fusion of Depth and Inertial Sensors", IEEE Sensors Journal, IEEE, USA, vol. 20, No. 3, Oct. 14, 2019 (Oct. 14, 2019), pp. 1445-1455, XP011767110.

Fuad Zain et al: "Human Action Recognition Using Fusion of Depth and Inertial Sensors", Jun. 6, 2018 (Jun. 6, 2018), SAT 2015 18th International Conference, Austin, TX, USA, Sep. 24-27, 2015; [Lecture Notes in Computer Science; Lect.Notes Computer], Springer, Berlin, Heidelberg, pp. 373-380, XP047476030.

Sinno Jialin Pan et al: "A Survey on Transfer Learning", IEEE Transactions On Knowledge and Data Engineering, IEEE Service Centre , Los Alamitos, CA, US, vol. 22, No. 10, Oct. 1, 2010 (Oct. 1, 2010), pp. 1345-1359, XP011296423, ISSN: 1041-4347.

* cited by examiner

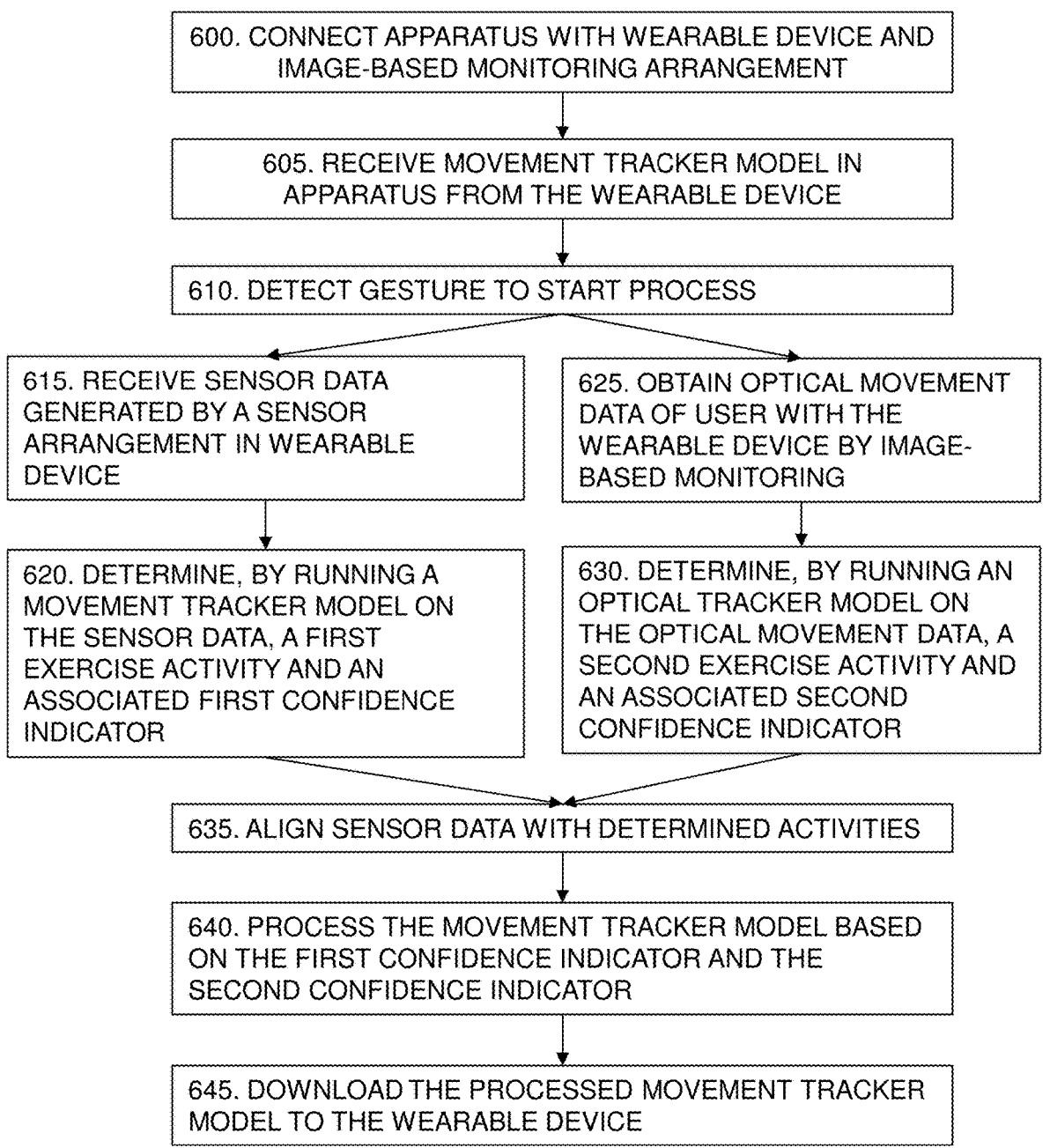

600. CONNECT APPARATUS WITH WEARABLE DEVICE AND IMAGE-BASED MONITORING ARRANGEMENT

605. RECEIVE MOVEMENT TRACKER MODEL IN APPARATUS FROM THE WEARABLE DEVICE

610. DETECT GESTURE TO START PROCESS

615. RECEIVE SENSOR DATA GENERATED BY A SENSOR ARRANGEMENT IN WEARABLE DEVICE

625. OBTAIN OPTICAL MOVEMENT DATA OF USER WITH THE WEARABLE DEVICE BY IMAGE-BASED MONITORING

620. DETERMINE, BY RUNNING A MOVEMENT TRACKER MODEL ON THE SENSOR DATA, A FIRST EXERCISE ACTIVITY AND AN ASSOCIATED FIRST CONFIDENCE INDICATOR

630. DETERMINE, BY RUNNING AN OPTICAL TRACKER MODEL ON THE OPTICAL MOVEMENT DATA, A SECOND EXERCISE ACTIVITY AND AN ASSOCIATED SECOND CONFIDENCE INDICATOR

635. ALIGN SENSOR DATA WITH DETERMINED ACTIVITIES

640. PROCESS THE MOVEMENT TRACKER MODEL BASED ON THE FIRST CONFIDENCE INDICATOR AND THE SECOND CONFIDENCE INDICATOR

645. DOWNLOAD THE PROCESSED MOVEMENT TRACKER MODEL TO THE WEARABLE DEVICE

Fig. 6

700. TRANSMIT MOVEMENT TRACKER MODEL TO APPARATUS FOR CONFIGURING THE WEARABLE DEVICE FOR EXERCISE TRACKING

705. TRANSMIT SENSOR DATA TO THE APPARATUS

710. RECEIVE PROCESSED MOVEMENT TRACKER MODEL FROM THE APPARATUS

715. RECEIVE PROCESSED MOVEMENT TRACKER MODEL DATA FROM THE APPARATUS

DEVICES AND METHODS FOR CONFIGURING A WEARABLE DEVICE FOR EXERCISE TRACKING

CROSS REFERENCE TO RELATED APPLICATIONS

The present application claims priority to Swedish patent application 2151364-3, filed Nov. 8, 2021, the content of which is incorporated herein by reference in its entirety.

TECHNICAL FIELD

The present disclosure relates generally to techniques for exercise tracking and, in particular, to improving performance of exercise tracking in a wearable device.

BACKGROUND

Physical exercise is deemed to be a relevant health factor, and for many people an important part of life. There are many popular forms of physical exercise including, for example, running, bicycling, and strength training. The growing interest in strength training is reflected by the growing number of gyms found in both public and private settings. Gyms may offer possibilities for weight training in machines or by use of free weights, as well as body weight training and group training in gym classes. There are also numerous websites and applications running on wireless devices that can assist users in managing their exercise.

One frequently used method for managing exercise activity is to detect and measure performance of various activities and motions. Data collected by various types of applications and devices may be processed and visualized, and used to determine progress with regard to plans or targets. In its simplest form, time-keeping by means of a clock provides an example of such data, e.g. for run training. Further types of methods and devices for collecting data associated with an exercise activity include inter alia pulse sensors, step counters, cadence meters, weight sensors etc.

Wearable devices for exercise tracking, sometimes referred to as fitness trackers, offer one way of measuring activities with the extra advantage of working both in- and outdoors and without fixed installations. Such a wearable device may comprise a sensor arrangement with one or more sensors configured to collect sensor data. Typically, the sensor arrangement comprises one or more accelerometers, configured to detect movement by sensing acceleration. The wearable device may further comprise or be connectable to logic configured to determine an identified exercise activity based on the sensor data. This may involve executing a movement tracker model on the sensor data to determine the exercise activity. In general, running a model on the wireless device speeds up processing and avoids latency issues that e.g. a device-to-cloud roundtrip would incur. Additionally, it naturally minimizes concerns of privacy issues by not sending personal information over a network to any other processing unit. In the case of accelerometer data, processing on the device avoids power and bandwidth issues by not transferring significant amounts of data over a network.

However, one disadvantage is that the models running on wearables need to rely on sensor data, such as accelerometer data, and can require calibration for activity recognition and for learning new types of exercise activities.

SUMMARY

It is an objective to at least partly overcome one or more limitations of the prior art. Another objective is to provide a technique of facilitating configuring of a wearable device for exercise tracking, in particular for improving activity type recognition. One or more of these objectives, as well as further objectives that may appear from the description below, are at least partly achieved by methods and devices according to the independent claims, embodiments thereof being defined by the dependent claims.

According to a first aspect, an apparatus is provided for configuring a wearable device for exercise tracking, the apparatus comprising:

a data storage unit, for storing sensor data generated by a sensor arrangement in the wearable device based on sensed movement of the wearable device, and optical movement data comprising representations of an individual obtained from an image-based monitoring system; and a processing unit configured to:

execute a movement tracker model on the sensor data to determine a first exercise activity and an associated first confidence indicator;

execute an optical tracker model on the optical movement data to determine a second exercise activity and an associated second confidence indicator;

process the movement tracker model based on the first confidence indicator and the second confidence indicator.

According to a second aspect, a method is provided for configuring a wearable device for exercise tracking, comprising:

receiving sensor data generated by a sensor arrangement in the wearable device based on sensed movement of the wearable device;

determining, by running a movement tracker model on the sensor data, a first exercise activity and an associated first confidence indicator;

obtaining optical movement data from an image-based monitoring system detecting representations of an individual, concurrently with the sensor arrangement obtaining the sensor data;

determining, by running an optical tracker model on the optical movement data, a second exercise activity and an associated second confidence indicator;

processing the movement tracker model based on the first confidence indicator and the second confidence indicator.

According to a third aspect, a wearable device for exercise tracking is provided, comprising:

a sensor arrangement configured to generate sensor data based on sensed movement of the wearable device;

a data storage unit for storing the sensor data and a movement tracker model;

a wireless transceiver unit; and a processing unit configured to execute the movement tracker model on the sensor data to determine an exercise activity;

wherein the processing unit is further configured to control the wireless transceiver unit to:

transmit the movement tracker model to an apparatus for configuring the wearable device for exercise tracking;

transmit the sensor data to the apparatus;

receive processed movement tracker model data from the apparatus based on optical movement data from an image-based monitoring system detecting representations of an individual concurrently with the sensor arrangement obtaining the sensor data; and wherein the processing unit is further configured:

update the movement tracker model on the in the data storage unit based on the processed movement tracker model data.

According to a fourth aspect, a system is provided for configuring a wearable device for exercise tracking, the exercise processing device comprising:

an image-based monitoring system configured to generate a time series of representations of an individual in the gym environment, wherein each of the representations defines a pose of the individual and comprises positions of a plurality of predefined feature points of the individual in a coordinate system; and an apparatus according to the first aspect.

Still other objectives, as well as features, aspects and technical effects will appear from the following detailed description, from the attached claims as well as from the drawings.

BRIEF DESCRIPTION OF THE DRAWINGS

Embodiments will now be described in more detail with reference to the accompanying schematic drawings.

FIG. 6 shows a flowchart comprising various steps included in a method for configuring the wearable device for exercise tracking as carried out in the apparatus according to various embodiments of the proposed solution.

DETAILED DESCRIPTION

Figure 1:
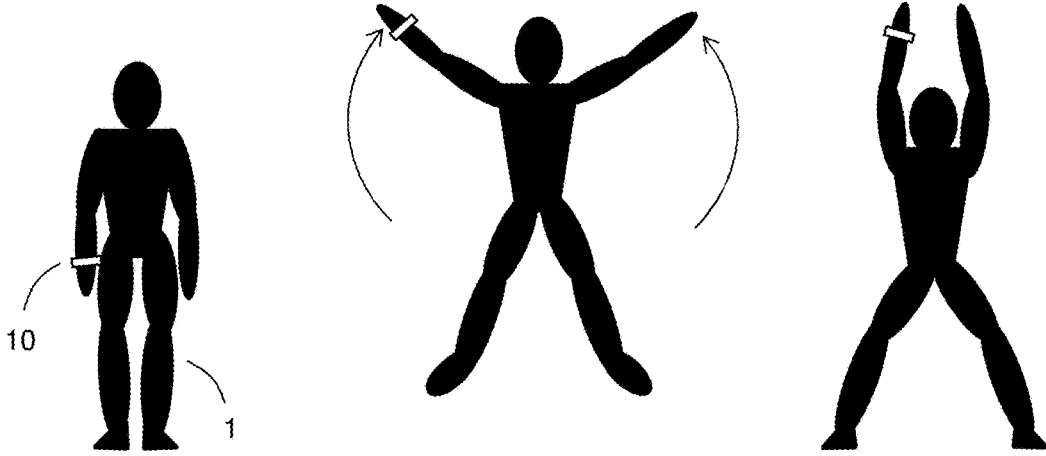
FIG. 1 schematically illustrates a user performing an exercise activity, while carrying a wearable device configured to for exercise tracking.

Embodiments will now be described more fully hereinafter with reference to the accompanying drawings, in which some, but not all, embodiments are shown. Indeed, the subject of the present disclosure may be embodied in many different forms and should not be construed as limited to the embodiments set forth herein; rather, these embodiments are provided so that this disclosure may satisfy applicable legal require-ments.

Also, it will be understood that, where possible, any of the advantages, features, functions, devices, and/or operational aspects of any of the embodiments described and/or contemplated herein may be included in any of the other embodiments described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, the terms "multiple", "plural" and "plurality" are intended to imply provision of two or more items, whereas the term a "set" of items is intended to imply a provision of one or more items. The term "and/or" includes any and all combinations of one or more of the associated listed items. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments. The term "compute", and derivatives thereof, is used in its conventional meaning and may be seen to involve performing a calculation involving one or more mathematical operations to produce a result, for example by use of a computer.

It will furthermore be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present disclosure. Well-known functions or constructions may not be described in detail for brevity and/or clarity. Unless otherwise defined, all terms (including technical and scientific terms) used herein have the same meaning as commonly understood by one of ordinary skill in the art to which this disclosure belongs. Like numbers refer to like elements throughout.

The proposed solution is related to enabling or improving the capability of tracking exercise activities using a wearable device which incorporates a model for determining exercise activity.

FIG. 1 schematically illustrates a user 1 carrying (or wearing) a wearable device 10. In the drawing, the user 1 carries out an exercise activity, e.g. so-called jumping jacks, wherein the wearable device 10 is configured to sense movement and generate movement data.

Figure 2A:
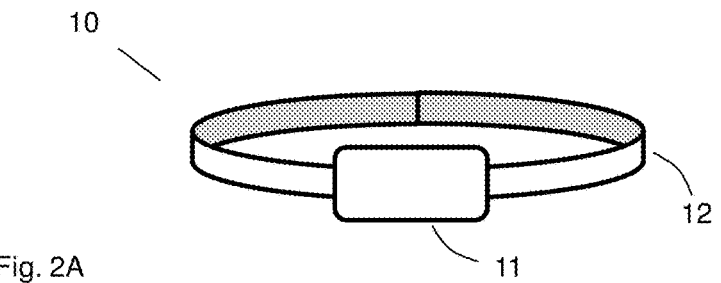
FIG. 2A schematically illustrates wearable device configured to for exercise tracking according to one example.

FIG. 2A schematically illustrates an example the wearable device 10. In this example, the wearable device 10 comprises an electronic unit 11 arranged with a connector member 12 for connecting the wearable device 10 to the user 1, which connector member 12 forms an armband or bracelet 12 configured to be worn on the wrist. It shall be noted, though, that when the wearable device 10 is discussed herein, the connector member 12 may be other than an armband, and may thus alternatively or additionally comprise a clip for attachment to a clothing or to a body part, or be incorporated within a piece of garment, a belt, in a shoe etc. Alternative arrangements of the connector member 12 are plausible.

Figure 2B:
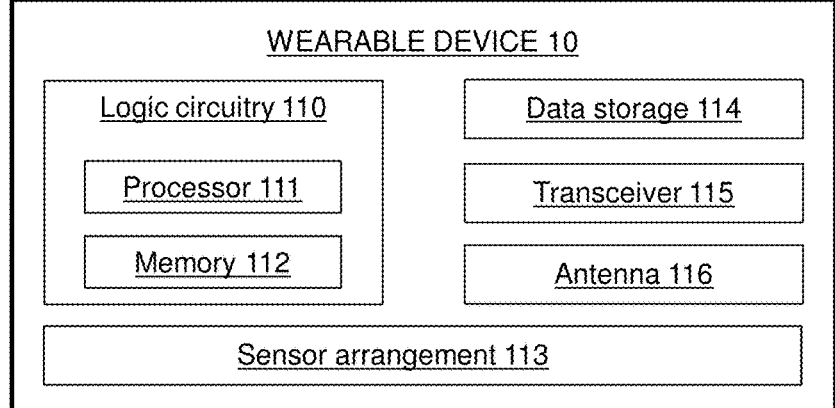
FIG. 2B illustrates functional elements of the wearable device of FIG. 2A.

FIG. 2B illustrates functional elements of an embodiment of the wearable device 10. The wearable device 10 comprises logic circuitry 110 configured to control operation of the wearable device 10, including storing and processing of sensor data to determine an exercise activity. The logic circuitry 110 may include a processing device 111, including one or multiple processors, microprocessors, data processors, co-processors, and/or some other type of component that interprets and/or executes instructions and/or data. The processing device 111 may be implemented as hardware (e.g., a microprocessor, etc.) or a combination of hardware and software (e.g., a system-on-chip (SoC), an application-specific integrated circuit (ASIC), etc.). The processing device 111 may be configured to perform one or multiple operations based on an operating system and/or various applications or programs.

The logic circuitry 110 may further include memory storage 112, which may include one or multiple memories and/or one or multiple other types of storage media. For example, the memory storage 112 may include a random access memory (RAM), a dynamic random access memory (DRAM), a cache, a read only memory (ROM), a programmable read only memory (PROM), flash memory, and/or some other type of memory.

The memory storage 112 is configured for holding computer program code, which may be executed by the processing device 111, wherein the logic circuitry 110 is configured to control the wearable device 10 to carry out any of the method steps as provided herein. Software defined by said computer program code may include an application or a program that provides a function and/or a process. The software may include device firmware, an operating system (OS), or a variety of applications that may execute in the logic circuitry 110.

The wearable device 10 further comprises a sensor arrangement 113, configured to sense movement of the wearable device 10. The sensor arrangement 113 may comprise one or more accelerometers, gyroscope units, inertial measurement units or the like. Such types of sensor arrangements are as such well-known, and are not described in further detail herein. It may nevertheless be noted that the sensor arrangement 113 is configured to generate sensor data based on its movement, e.g. caused by a user 1 wearing the wearable device 10, such as accelerometer data. The sensor data may comprise a series of sensor values and associated time stamps referring to when the sensor value was detected, which time stamps may be taken using a local clock unit, e.g. provided in the logic circuitry 110 or in the sensor arrangement 113 itself. Each sensor value may comprise vector data which correlates with a level of magnitude and a direction of movement with respect to a local coordinate system of the wearable device 10.

The wearable device 10 further comprises a data storage unit 114, configured to hold the sensor data generated by the sensor arrangement 113. The data storage unit 114 is further configured to store a movement tracker model, executable by the processor 11 of the logic circuitry 110. The movement tracker model may comprise computer code and instructions realizing a machine-learning algorithm, configured to take the sensor data as input to determine an exercise activity. This may involve identifying a series of movements, based on the sensor values and associated time stamps, and correlating the series of movements with a plurality of prestored exercise movement patterns to identify an exercise activity.

The movement tracker model may comprise a machine-learning algorithm configured to take sensor data, such as accelerometer and gyroscope data, and divide such continuous data into segments of certain lengths. Furthermore, the machine-learning algorithm may pre-process or transform sensor data using any processing such as denoising, structural, or statistical transformations. The machine-learning algorithm may use one or models trained to infer the exercise activity corresponding to a segment of sensor data. The machine-learning model may be of any type including, for example, Random Forest, Support Vector Machine, or Deep Neural Networks.

The wearable device 10 further comprises a wireless transceiver unit 11, which may comprise a plurality of different signal transceivers, such as radio transceivers, for communicating with various entities of a system, such as an apparatus 20 adapted for configuring the wearable device 10 as will be described, and possibly with a radio communication network. The wireless transceiver unit 11 may thus include a radio receiver and transmitter for communicating through at least an air interface. As an example, the wireless transceiver unit 11 may comprise one or more short range devices, such as a Bluetooth Low Energy (BLE) device, a wireless local area network (WLAN) transceiver, and potentially a wide area network (WAN) transceiver, e.g. for communication in a cellular network.

The wearable device 10 further comprises a power supply (not shown), e.g. a battery. The wearable device 10 may optionally further comprise a user interface, such as a display and/or an audio interface, for allowing a user 1 to operate the wearable device 10.

Due to several reasons, it may be challenging to make a proper determination of exercise activity using the movement tracker model in the wearable device 10. For one thing, the wearable device 10 will only detect the movements caused on the sensor arrangement 113, and thus only to the part of the user 1 where the wearable device is connected. It may be noted, though, that in various embodiments, the sensor arrangement 113 may comprise a plurality of distributed sensor units, connectable to different parts of the user, such as configured in more than one or of the mentioned alternatives: armband, garment, belt, shoe etc. Nevertheless, user movement may be complex, and in addition, several types of different exercise activities may generate similar sensor data.

The proposed solution provides an improvement in the field of configuring the wireless device to properly identify an exercise activity. Broadly speaking, this is obtained by taking input from another source of input data, collected concurrently with the sensor data, to process the movement tracker model so as to improve its capability of determining an exercise activity, i.e. to identify a type of exercise activity. Specifically, optical movement data, comprising representations of the user 1 obtained from an image-based monitoring system, is used to make an additional identification of an executed exercise activity, which is correlated with the exercise activity determined based on the sensor data. Dependent on these at least two different determinations of the exercise activity, the movement tracker model may be updated, or retrained.

Figure 3:
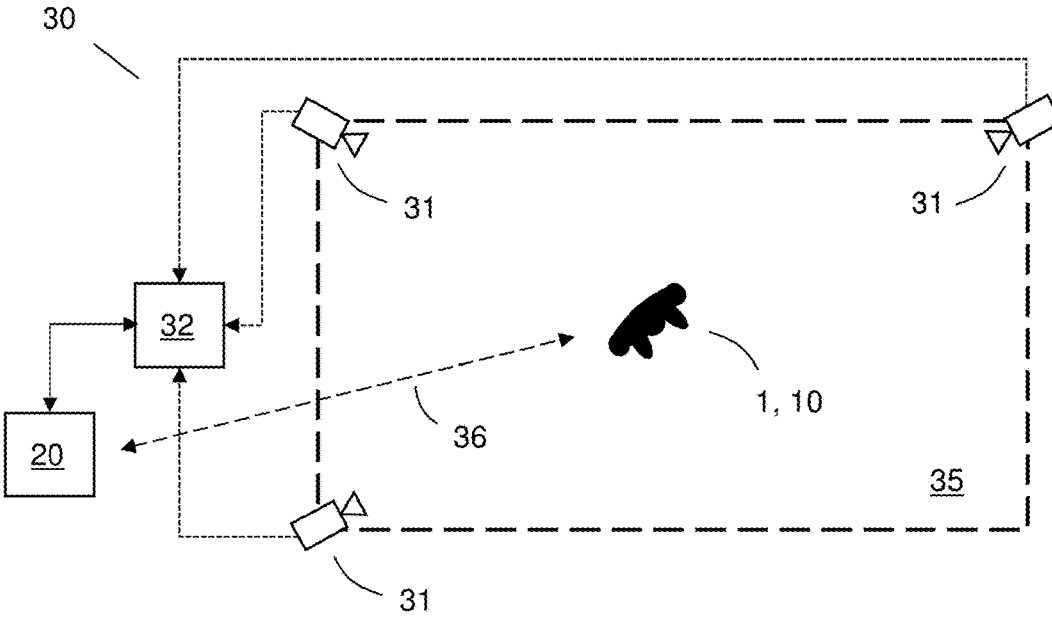
FIG. 3 schematically illustrates a system for configuring the wearable device for exercise tracking, which systems comprises an image-based monitoring system from which optical movement data is taken to determine retraining of a movement tracker model in the wearable device.

FIG. 3 schematically illustrates an image-based monitoring system 30 according to one example, usable in conjunction with the proposed solution, which arrangement 30 is configured to obtain optical input to generate optical movement data. This arrangement 30 comprises one or more image-capturing devices 31, such as digital cameras, configured to capture a series of images with associated time stamps. The image-based monitoring system 30 is in various embodiments established to monitor a gym environment, such as an area 35 in which one or more users may carry out a physical activity. A control system 32 is configured to take input of image data from the one or more image-capturing devices 31, and to identify human representations in the area 3, hereinafter referred to as a gym environment, and track movement of the human representations. The gym environment 35 may be a room, a series of rooms, a part of a room, or an outdoor area. The control system 32 is identified in the drawing as a single element for the sake of simplicity. It should be noted, though, that the control system 32 may completely or partly share resources with other elements of the system, such as one or more image-capturing devices 31. Alternatively, or additionally, the control system 32 may employ shared logic in a cloud arrangement.

The image-based monitoring system 30 is configured to detect presence of objects in the gym environment 35, and to identify an object as a human. By image detection and processing of the captured image data, using the one or more image-capturing devices 31, various key points of detected objects may be identified. Based on e.g. shape, size, correlated movement of key points, and other recognizable patterns, a detected object may be characterized as a human person. The combined key points of an object detected and characterized as a human person may be referred to as a human representation.

There are various ways of determining a human representation based on image data, and specifically based optical movement data comprising a time series of images having associated time stamps. In at least certain examples, a single time series of image data, obtained by a single image-capturing device 31, may be sufficient, meaning that processing of the optical movement data from a single image-capturing device 31 may be used to identify an exercise activity. Dependent on complexity, or similarity between different exercise activities, a plurality of image-capturing devices 31 may be useful to improve performance in recovering a position and pose of an object from a plurality of images, such as iterative still images or a video stream.

Before proceeding with description of additional features and functions of the proposed solution, a general presentation of various aspects of examples of the image-based monitoring system 30 will be discussed. For reference, applicant's own applications SE 2150238-0 and SE2150257-0 provide more extensive description of image-based monitoring to determine pose and position of a human, including how to assign collected image data to a certain user. The content of those applications are hereby incorporated by reference.

One solution known in the art is to use multiple cameras 31 with overlapping fields of view 20, where the position and orientation of the cameras 31 is known with reasonable accuracy, for example by measurement during installation. In operation, 3D positioning and pose determination typically comprises two stages: processing of individual video streams from the multiple cameras 31 for detection of objects and key points of the respective object, and processing the detections to identify correspondence between detections of the same object in different views and calculating the position and/or pose of the respective object based on the correspondence between detections, and optionally temporal information. There are several established techniques for performing the first stage with good performance, for example by use of convolutional neural networks.

As used herein, "key point" has its conventional meaning in the field of computer vision and is also known as an interest point. A key point is a spatial location or point in an image that define what is interesting or what stand out in the image and may be defined to be invariant to image rotation, shrinkage, translation, distortion, etc. More generally, a key point may be denoted a "reference point" on an object to be detected in the image, with the reference point having a predefined placement on the object. Key points may be defined for a specific type of object, for example a human body, a part of the human body, or an inanimate object with a known structure or configuration. In the example of a human body, key points may identify one or more joints and/or extremities. Key points may be detected by use of any existing feature detection algorithm(s), for example image processing techniques that are operable to detect one or more of edges, corners, blobs, ridges, etc. in digital images. Non-limiting examples of feature detection algorithms comprise SIFT (Scale-Invariant Feature Transform), SURF (Speeded Up Robust Feature), FAST (Features from Accelerated Segment Test), SUSAN (Smallest Univalue Segment Assimilating Nucleus), Harris affine region detector, and ORB (Oriented FAST and Rotated BRIEF). Further information about conventional key point detectors is found in the article "Local invariant feature detectors: a survey", by Tuytelaars et al, published in Found. Trends. Comput. Graph. Vis. 3(3), 177-280 (2007). Further examples of feature detection algorithms are found in the articles "Simple Baselines for Human Pose Estimation and Tracking", by Xiao et al, published at ECCV 2018, and "Deep High-Resolution Representation Learning for Human Pose Estimation", by Sun et al, published at CVPR 2019. Correspondingly, objects may be detected in images by use of any existing object detection algorithm(s). Non-limiting examples include various machine learning-based approaches or deep learning-based approaches, such as Viola—Jones object detection framework, SIFT, HOG (Histogram of Oriented Gradients), Region Proposals (RCNN, Fast-RCNN, Faster-RCNN), SSD (Single Shot MultiBox Detector), You Only Look Once (YOLO, YOLO9000, YOLOv3), and RefineDet (Single-Shot Refinement Neural Network for Object Detection).

As used herein, "pose" defines the posture of a human object and comprises a collection of positions which may represent key points. The positions may be two-dimensional (2D) positions, for example in an image coordinate system, resulting in a 2D pose, or three-dimensional (3D) positions, for example in a scene coordinate system, resulting in a 3D pose. A pose for a human object is also referred to as a "skeleton" herein.

Figure 4:
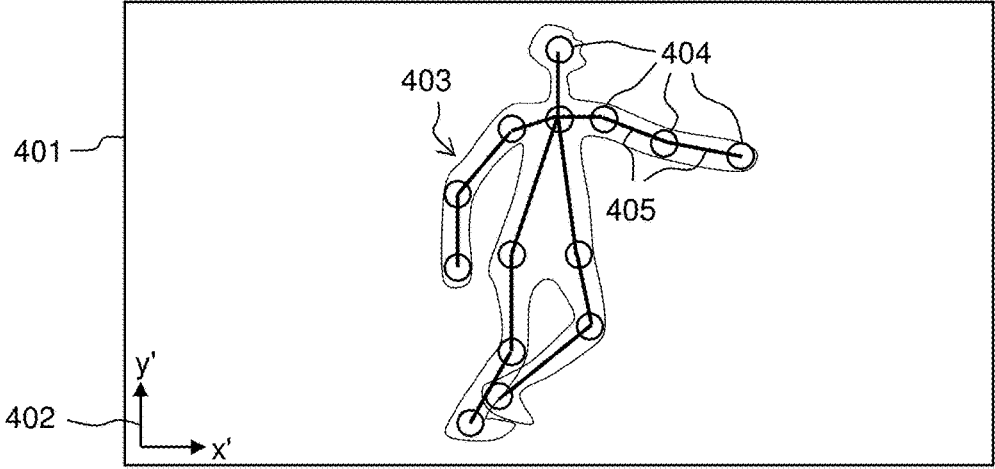
FIG. 4 schematically illustrates schematically depicts human representation of an individual 2D performing an exercise, based on input from the image-monitoring system.

FIG. 4 illustrates an example 2D image 401 taken by a camera 31 from a specific viewing angle. The image 101 includes a 2D representation 403 of the individual 1. The 2D representation 403 depicts a "2D pose" of the individual as seen from the viewing angle. The 2D pose is defined by predefined feature points, i.e. key points 404, which are connected by 2D links 405. The position of each key point is given by 2D coordinates $(x',y')$ in a local coordinate system 402 of the image/camera. As noted above, many established techniques for detection of key points are available.

A machine learning optical tracker model may be incorporated and executed in the control system 32 to identify an exercise activity based on the optical movement data. In some examples, this comprises determining a series of poses, with successive time stamps, which are identified as a movement. The identification of an exercise activity based on the optical movement data may involve determining one out of a plurality of predetermined, or learned, activity exercise by activity recognition, such as detecting and counting repetitions, weight, distance or the like, related to an exercise activity. This may involve identifying, and labeling, the determined exercise activity as one out of a plurality of previously stored or learned activities, such as walking, running, jumping jacks, push-ups, burpees etc. Confidence is determined from inference output given by the optical tracker model to generate an output comprising a label of the recognized exercise activity together with a probability score.

According to the solution proposed herein, exercise activity determination in a wearable device 10, including recognition and counting or measuring, is improved by making comparative analysis with concurrent exercise activity determination using the model of the wearable device based on sensor data, and exercise activity determination using the image-based monitoring system 30 based on optical movement data.

Figure 5:
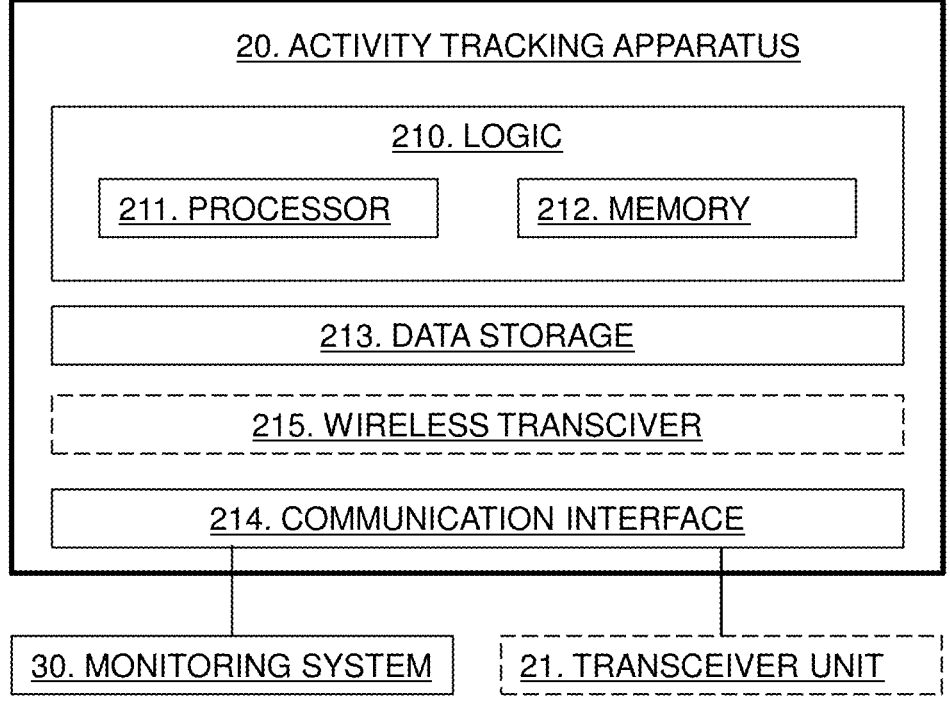
FIG. 5 illustrates functional blocks comprised in an apparatus configured to 4 schematically illustrates an example of an electronic device, arranged for configuring the wearable device for exercise tracking.

FIG. 5 illustrates an example of an apparatus 20 for configuring the wearable device 10 for exercise tracking, and for carrying out the method steps as outlined.

The apparatus 20 comprises logic 210 configured to control the various process steps and entities of the apparatus 20, including to communicate with other elements. The logic 210 may include a processing device 211, including one or multiple processors, microprocessors, data processors, co-processors, and/or some other type of component that interprets and/or executes instructions and/or data. The processing device 211 may be implemented as hardware (e.g., a microprocessor, etc.) or a combination of hardware and software (e.g., a system-on-chip (SoC), an application-specific integrated circuit (ASIC), etc.). The processing device 211 may be configured to perform one or multiple operations based on an operating system and/or various applications or programs.

The logic 210 may further include memory storage 212, which may include one or multiple memories and/or one or multiple other types of storage mediums. For example, the memory storage 212 may include a random access memory (RAM), a dynamic random access memory (DRAM), a cache, a read only memory (ROM), a programmable read only memory (PROM), flash memory, and/or some other type of memory. The memory storage 312 may include a hard disk (e.g., a magnetic disk, an optical disk, a magneto-optic disk, a solid state disk, etc.).

The memory storage 212 is configured for holding computer program code, which may be executed by the processing device 211, wherein the logic 210 is configured to control the apparatus 20 to carry out any of the method steps as provided herein. Software defined by said computer program code may include an application or a program that provides a function and/or a process. The software may include device firmware, an operating system (OS), or a variety of applications that may execute in the logic 210.

The apparatus 20 further comprises a data storage unit 213, configured to optical movement data generated by the image-based monitoring system 30. The data storage unit 213 is further configured to store an optical tracker model. The optical tracker model may comprise computer code and instructions realizing a machine-learning algorithm, configured to take the optical movement data as input to determine an exercise activity. This may involve identifying a series of movements, based on determined poses and associated time stamps, and correlating the series of poses with a plurality of prestored exercise movement patterns to identify an exercise activity.

The machine learning algorithm may be configured to determine the exercise activity using a pipeline of machine-learning models. This may involve identifying human key points, determining human poses and associated time stamps, and estimating exercise activity from the series of human poses. Alternatively, the machine-learning algorithm may be configured to jointly determine key point detection, human pose estimation, and exercise activity using a single end-to-end machine-learning model.

The apparatus 20 further comprises a communication interface 214, for communication with at least the image-based monitoring system 30, and possibly also with an external transceiver unit 21 for communicating with the wearable device 10. Alternatively, the apparatus 20 comprises a wireless transceiver 215, configured for communication with the wearable device 10. Communication with the wearable device 10 may be accomplished over a wireless link 36, as indicated in FIG. 3. The communication interface 214 may further provide connection to outside sources of communication, such as to the internet, for communicating data with a server (not shown) for holding exercise data.

The apparatus 20 further comprises a power supply (not shown), e.g. a battery or a mains connector. The apparatus 20 may optionally further comprise a user interface, such as a display and/or an audio interface, for allowing an operator to configure the apparatus 20.

It may be noted that various elements of the apparatus 20 may share resources with the image-based monitoring system 30, and particularly the control system 32, such as logic and/or memory. In various embodiments, the apparatus 20 forms part of the image-based monitoring system 30.

FIG. 6 illustrates a flowchart showing various steps included in a different examples of a method according to the proposed solution, as carried out by the apparatus 20 for configuring the wearable device 10 for exercise tracking.

According to one aspect, the method comprises:

Receiving 615 sensor data generated by a sensor arrangement 113 in the wearable device 10 based on sensed movement of the wearable device.

Determining 620, by running a movement tracker model on the sensor data, a first exercise activity and an associated first confidence indicator.

Obtaining 625 optical movement data from an image-based monitoring system 30 detecting representations of an individual 1, concurrently with the sensor arrangement obtaining the sensor data.

Determining 630, by running an optical tracker model on the optical movement data, a second exercise activity and an associated second confidence indicator;

Processing 640 the movement tracker model based on the first confidence indicator and the second confidence indicator.

The proposed solution improves functionality of the wearable device 10 by taking input from the image-based monitoring system 30 to enhance training of the movement tracker model. This way, the movement tracker model is configured to enhance its capability of properly identifying various exercise activities, whereby further exercise activity collection, e.g. for registering in a training app, using only the wearable device 10 is improved. Specifically, by using optical data collected with the image-based monitoring system in a gym environment 35, concurrently with the wearable device 10 collecting sensor data, the method may be carried out during a supervised exercise session. This way, the user 1 may be schooled to carry out the exercise in an intended fashion, which further increases the chances of properly mimicking the exercise activity at a later stage and identifying the exercise activity using only the trained movement tracker model in the wearable device 10.

An example scenario of the proposed solution will now be described in further detail with reference to the drawings, and particularly to FIG. 6. It shall be noted, though, that the various steps and features of this example are not restricted to this particular scenario, which is rather presented to provide an easily understandable context.

In step 600, a user 1 enters a gym facility, while carrying a wearable device 10. The wearable device 10 connects to a monitoring system of the gym facility, which monitoring system comprises an image-based monitoring system 30 which covers a gym area 35. Connection may be triggered by tap in registering, e.g. using short range communication such as NFC between a wireless transceiver 115 of the wearable device 10 and the wireless transceiver 215, 21 of the apparatus 20. Alternatively, the connection may be triggered by the wearable device automatically connecting via another wireless medium, such as BLE or Wifi, once the wearable device 10 is in communication range with the apparatus 20. In yet another alternative, the user 1 may be required to actively trigger the connection, e.g. by UI input on the wearable device 10 or on a user interface (not shown) connected to the apparatus 20.

Once connected, the wearable device uploads 605 its movement tracker model from local storage 114 to the apparatus 20, for storage in the data storage 213. This may be obtained over the wireless link 36.

In some examples, the beginning of a training session, during which the movement tracker model is to be trained by input from the optical movement data, may be initiated and triggered by the user 1 making a special gesture, which is detected 610 by both the wearable device 10 and the image-based monitoring system 30. This may be used by the image-based monitoring system 30 to properly identify the human representation 403, or skeleton, in the gym area 35, to which data obtained from the sensor arrangement 113 of the wearable device 10 is to be processed.

In step 615, the sensor arrangement 113 collects movement data, e.g. accelerometer data, generated by the movement of the wearable device 10, and transmits it to the apparatus 20. In some examples, the wearable device 10 is configured to stream the sensor data over the wireless link 36 to the apparatus during the exercise session. Alternatively, the sensor data is collected, and uploaded after the exercise session is terminated.

In step 620, the apparatus 20 runs the movement tracker model on the received sensor data to determine a first exercise activity and an associated first confidence indicator. Determining the first exercise activity may comprise detecting and identifying a first activity type, and to count one or more activities, e.g. repetitions within that activity type.

In step 625, at least one camera 31 of the image-based monitoring system collects a time series of images, concurrently with the sensor arrangement 113 collecting sensor data.

In step 630, visual activity recognition, detection and counting is carried out, in the image-based monitoring system 30 or in the apparatus 20. This may involve determining optical movement data comprising identifying a time series of data associated with identified key points and related poses. By running an optical tracker model on the optical movement data, a second exercise activity and an associated second confidence indicator is determined.

In step 635, where the wearable device 10 is not synchronized to operate on a common clock signal as the apparatus, the received sensor data is aligned with the activities detected by both the image-based monitoring system 30 and the movement tracker model. This may involve aligning first time stamp data of the sensor data with second time stamp data of the optical movement data to obtain a time aligned correlation between the determined first exercise activity and the determined second exercise activity.

In step 640, the apparatus is configured to process the movement tracker model based on the first confidence indicator and the second confidence indicator. In some embodiments, this involves retraining the movement tracker model, based on comparison between the first confidence indicator and the second confidence indicator.

According to one aspect, where sections of the exercise session in which the optical tracker model, based on image-based activity recognition, is identified as being more confident in activity determination than the movement tracker model, such sections may be used for retraining the movement tracker model.

Confidence is determined from inference output given by both image-based exercise activity determination based on the optical movement data, and the exercise activity determination based on the sensor data. The output of each confidence determination, i.e. the confidence indicator, may comprise a label identifying the recognized activity together with a probability score. In some examples, higher confidence may correlate with, or be defined by, a higher probability score.

Processing the tracker model may thus comprise retraining the tracker model to identify the second exercise activity based on said sensor data, responsive to the second exercise activity being different from the first exercise activity.

According to one example, if the movement tracker model is more confident than the optical tracker model, no retraining is done. The processing step 640 may thus comprise comparing the first confidence indicator with the second confidence indicator, wherein retraining of the tracker model is carried out responsive to the second confidence indicator indicating higher confidence than the first confidence indicator.

In various embodiments, a higher trust is placed on the optical movement model, taking input from the image-based monitoring system 30, than on the movement tracker model taking sensor data as input. The reason for this is that the image-based monitoring system 30 is configured to detect and recognize activity of substantially the whole individual 1, whereas the wearable device 10 takes input only from movement of a single, or a view, parts of the individual user 1. In such an example, the apparatus may be configured such that if the confidence indicator obtained from the optical movement model meets or exceeds a certain value, the apparatus will retrain the movement tracker model even if the confidence indicator obtained by the movement tracker model is higher. As an example, assume that the movement tracker model identifies a label of "boxing" with a probability score of 95%, while the optical tracker model identifies a label of "running" with a probability score of 90%. If the probability score 90% exceeds a predetermined threshold of 85% the sensor data collected and used in the determination by the movement tracker model will be used for retraining the movement tracker model for the purpose of identifying running.

Accordingly, in some embodiments, the processing 640 may comprise comparing the first confidence indicator with the second confidence indicator, wherein retraining of the tracker model is carried out responsive to the second confidence indicator indicating higher confidence than the first confidence indicator or higher than a prestored confidence indicator.

Processing the movement tracker model may thus comprise retraining. This may comprise updating using incremental learning, using the received sensor data and the inference obtained from the optical tracker model, running image-based activity recognition.

At the end of a training session, for example at a locker room area, the apparatus 20 uploads the model to the wearable device, at least when the movement tracker model has been retrained. The method may thus comprise downloading 645 the processed movement tracker model to the wearable device. In this context it may be noted that in one example, the processing unit 111 of the wearable device 10 may be configured to update the movement tracker model in the data storage unit based on received 645 processed movement tracker model data. Alternatively, the processed movement tracker model data may comprise an updated version of the transmitted movement tracker model.

Figure 7:
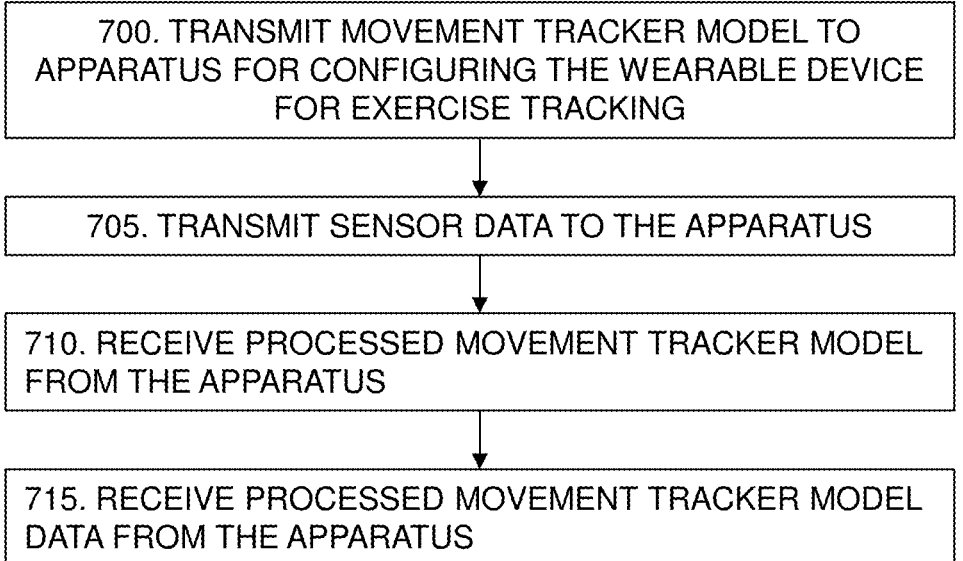
FIG. 7 shows a flowchart comprising various steps included in a method for configuring the wearable device for exercise tracking as carried out in the wearable device according to various embodiments of the proposed solution.

FIG. 7 schematically illustrates various steps that may be carried out by the wearable device 10 in accordance with one aspect of the proposed solution.

In step 700, the processing unit 111 of the wearable device transmits the movement tracker model to an apparatus 20 for configuring the wearable device for exercise tracking.

In step 705 the processing unit 111 transmit sensor data to the apparatus by using a wireless transceiver 115, which sensor data is generated by a sensor arrangement 113 configured to sense movement of the wearable device.

In step 710, the wearable device receives 710 processed movement tracker model data from the apparatus based on optical movement data from an image-based monitoring system detecting representations of an individual concurrently with the sensor arrangement obtaining the sensor data.

In step 715 the processing unit 111 is configured to update the movement tracker model in the data storage unit of the wearable device 10 based on the processed movement tracker model data. The processed movement tracker model data may be data for use by the processing unit 111 to reconfigure the movement tracker model. Alternatively, the processed movement tracker model data may comprise an updated version of the transmitted movement tracker model.

In the foregoing, the proposed solution has been described with reference to the drawings, including various examples and alternative embodiments. the proposed solution provides the technical effect of improving exercise activity determination in a wearable device, by adaptation based on a supporting image-based monitoring system.

One beneficial aspect of the proposed solution is that multiple gyms (with respective areas 35) may participate in retraining a better model for the wearable device 10. The proposed solution provides a way for the wearable device 10, i.e. its movement tracker model, to conveniently learn new activities. The proposed solution also allows for improved activity recognition due to supervised learning using a more powerful visual (optical) activity recognition system. Moreover, heavy retraining of the movement tracker model is offloaded to a power-supplied device, i.e. the apparatus 20. The proposed solution may take any shape or form as provided herein, and as outlined in the appended claims and in the items listed below.

Item 1. An apparatus (20) for configuring a wearable device (10) for exercise tracking, the apparatus comprising:
a data storage unit (213), for storing sensor data generated by a sensor arrangement in the wearable device based on sensed movement of the wearable device, and optical movement data comprising representations of an individual obtained from an image-based monitoring system (30); and
a processing unit (211) configured to:
execute a movement tracker model on the sensor data to determine a first exercise activity and an associated first confidence indicator;
execute an optical tracker model on the optical movement data to determine a second exercise activity and an associated second confidence indicator;
process the movement tracker model based on the first confidence indicator and the second confidence indicator.

Item 2. The apparatus of Item 1, comprising:
a wireless communication unit (214, 215) for receiving the sensor data and movement tracker model from the wearable device.

Item 3. The apparatus of Item 2, wherein the processing unit is configured to transmit processed movement tracker model data to the wearable device using the wireless communication unit.

Item 4. The apparatus of any preceding Item, comprising:
a data input unit (214) for obtaining said optical movement data.

Item 5. The apparatus of any preceding Item, wherein the processing unit is configured to:
align first time stamp data of the sensor data with second time stamp data of the optical movement data to obtain a time aligned correlation between the determined first exercise activity and the determined second exercise activity.

Item 6. The apparatus of any preceding Item, wherein the processing unit is configured to:
retrain the tracker model to identify the second exercise activity based on said sensor data, responsive to the second exercise activity being different from the first exercise activity.

Item 7. The apparatus of Item 6, wherein processing unit is configured to:
compare the first confidence indicator with the second confidence indicator; and
to retrain of the tracker model responsive to the second confidence indicator indicating higher confidence than the first confidence indicator.

Item 8. The apparatus of Item 6, wherein processing unit is configured to:
compare the first confidence indicator with the second confidence indicator; and
to retrain of the tracker model responsive to the second confidence indicator indicating higher confidence than the first confidence indicator or higher than a prestored confidence indicator.

Item 9. The apparatus of any preceding Item, wherein each confidence indicator comprises a probability score.

Item 10. A method for configuring a wearable device for exercise tracking, comprising:
receiving (615) sensor data generated by a sensor arrangement in the wearable device based on sensed movement of the wearable device;
determining (620), by running a movement tracker model on the sensor data, a first exercise activity and an associated first confidence indicator;
obtaining (625) optical movement data from an image-based monitoring system detecting representations of an individual, concurrently with the sensor arrangement obtaining the sensor data;
determining (630), by running an optical tracker model on the optical movement data, a second exercise activity and an associated second confidence indicator;
processing (640) the movement tracker model based on the first confidence indicator and the second confidence indicator.

Item 11. The method of Item 10, comprising:
receiving (605) the movement tracker model in an apparatus by upload from the wearable device, wherein the movement tracker and the optical tracker model are run in the apparatus.

Item 12. The method of Item 11, comprising:
downloading (645) the processed movement tracker model to the wearable device.

Item 13. The method of any of Items 10-12, comprising:

aligning (635) first time stamp data of the sensor data with second time stamp data of the optical movement data to obtain a time aligned correlation between the determined first exercise activity and the determined second exercise activity.

Item 14. The method of any of Items 10-13, wherein processing the tracker model comprises:

retraining the tracker model to identify the second exercise activity based on said sensor data, responsive to the second exercise activity being different from the first exercise activity.

Item 15. The method of Item 14, wherein processing the tracker model comprises:

comparing the first confidence indicator with the second confidence indicator;

wherein retraining of the tracker model is carried out responsive to the second confidence indicator indicating higher confidence than the first confidence indicator.

Item 16. The method of Item 14, wherein processing the tracker model comprises:

comparing the first confidence indicator with the second confidence indicator;

wherein retraining of the tracker model is carried out responsive to the second confidence indicator indicating higher confidence than the first confidence indicator or higher than a prestored confidence indicator.

Item 17. The method of any of Items 10-16, wherein each confidence indicator comprises a probability score.

Item 18. A wearable device (10) for exercise tracking, comprising:

a sensor arrangement (113) configured to generate sensor data based on sensed movement of the wearable device;

a data storage unit (114) for storing the sensor data and a movement tracker model;

a wireless transceiver unit (115); and a processing unit (111) configured to execute the movement tracker model on the sensor data to determine an exercise activity;

wherein the processing unit (111) is further configured to control the wireless transceiver unit to:

transmit the movement tracker model to an apparatus for configuring the wearable device for exercise tracking;

transmit the sensor data to the apparatus;

receive processed movement tracker model data from the apparatus based on optical movement data from an image-based monitoring system detecting representations of an individual concurrently with the sensor arrangement obtaining the sensor data; and wherein the processing unit is configured to:

update the movement tracker model on the in the data storage unit based on the processed movement tracker model data.

Item 19. A system for configuring a wearable device (10) for exercise tracking, the exercise processing device comprising:

an image-based monitoring system (30) configured to generate a time series of representations of an individual in the gym environment, wherein each of the representations defines a pose of the individual and comprises positions of a plurality of predefined feature points of the individual in a coordinate system; and an apparatus (20) according to any of Items 1-9.

The invention claimed is:

1. An apparatus for configuring a wearable device for exercise tracking, the apparatus comprising:

a data storage unit, for storing sensor data including at least one of accelerometer data, gyroscope data, or inertial measurement data, generated by a sensor arrangement in the wearable device based on sensed movement of the wearable device, and optical movement data comprising representations of an individual obtained from an image-based monitoring system; and a processing unit configured to:

execute a movement tracker model on the sensor data to determine a first exercise activity and an associated first confidence indicator;

execute an optical tracker model on the optical movement data to determine a second exercise activity and an associated second confidence indicator;

retrain the movement tracker model to identify the second exercise activity based on the sensor data according to a comparison of the first confidence indicator and the second confidence indicator.

2. The apparatus of claim 1, comprising:

a wireless communication unit for receiving the sensor data and movement tracker model from the wearable device.

3. The apparatus of claim 2, wherein the processing unit is configured to transmit processed movement tracker model data to the wearable device using the wireless communication unit.

4. The apparatus of claim 1, comprising:

a data input unit for obtaining said optical movement data.

5. The apparatus of claim 1, wherein the processing unit is configured to:

align first time stamp data of the sensor data with second time stamp data of the optical movement data to obtain a time aligned correlation between the determined first exercise activity and the determined second exercise activity.

6. The apparatus of claim 1, wherein the second exercise activity is different from the first exercise activity.

7. The apparatus of claim 1, wherein processing unit is configured to:

compare the first confidence indicator with the second confidence indicator, wherein the movement tracker model is retrained responsive to the second confidence indicator indicating a higher confidence than the first confidence indicator.

8. The apparatus of claim 1, wherein the movement tracker model is retrained responsive to the second confidence indicator indicating a higher confidence than a prestored confidence indicator.

9. The apparatus of claim 1, wherein each confidence indicator comprises a probability score.

10. A system for configuring a wearable device for exercise tracking, the exercise processing device comprising:

an image-based monitoring system configured to generate a time series of representations of an individual in the gym environment, wherein each of the representations defines a pose of the individual and comprises positions of a plurality of predefined feature points of the individual in a coordinate system; and the apparatus according to claim 1.

11. The apparatus of claim 1, wherein, when the second confidence indicator indicating a confidence higher than a prestored threshold value, the processing unit is further configured to retrain the movement tracker model to identify the second exercise activity based on the sensor data even if the first confidence indicator indicates a higher confidence than the second confidence indicator.

12. A method for configuring a wearable device for exercise tracking, comprising:

receiving sensor data including at least one of accelerometer data, gyroscope data, or inertial measurement data, generated by a sensor arrangement in the wearable device based on sensed movement of the wearable device;

determining, by running a movement tracker model on the sensor data, a first exercise activity and an associated first confidence indicator;

obtaining optical movement data from an image-based monitoring system detecting representations of an individual, concurrently with the sensor arrangement obtaining the sensor data;

determining, by running an optical tracker model on the optical movement data, a second exercise activity and an associated second confidence indicator; and retraining the movement tracker model to identify the second exercise activity based on the sensor data according to a comparison of the first confidence indicator and the second confidence indicator.

13. The method of claim 12, comprising:

receiving the movement tracker model in an apparatus by upload from the wearable device, wherein the movement tracker and the optical tracker model are run in the apparatus.

14. The method of claim 13, comprising:

downloading the processed movement tracker model to the wearable device.

15. The method of claim 12, comprising:

aligning first time stamp data of the sensor data with second time stamp data of the optical movement data to obtain a time aligned correlation between the determined first exercise activity and the determined second exercise activity.

16. The method of claim 12, wherein the second exercise activity is different from the first exercise activity.

17. The method of claim 12, further comprising comparing the first confidence indicator with the second confidence indicator;

wherein the movement tracker model is retrained responsive to the second confidence indicator indicating a higher confidence than the first confidence indicator.

18. The method of claim 12, wherein processing the tracker model comprises:

wherein the movement tracker model is retrained responsive to the second confidence indicator indicating a higher confidence than a prestored confidence indicator.

19. The method of claim 12, wherein each confidence indicator comprises a probability score.

20. A wearable device for exercise tracking, comprising:

a sensor arrangement configured to generate sensor data, including at least one of accelerometer data, gyroscope data, or inertial measurement data, based on sensed movement of the wearable device;

a data storage unit for storing the sensor data and a movement tracker model;

a wireless transceiver unit; and a processing unit configured to execute the movement tracker model on the sensor data to determine a first exercise activity and a first confidence indicator;

wherein the processing unit is further configured to control the wireless transceiver unit to:

transmit the movement tracker model to an apparatus for configuring the wearable device for exercise tracking;

transmit the sensor data, the first exercise activity and the first confidence indicator to the apparatus;

receive processed movement tracker model data from the apparatus obtained by retraining the movement tracker model based on a comparison of the first exercise activity and first confidence indicator together with a second exercise activity and a second confidence indicator based on optical movement data from an image-based monitoring system detecting representations of an individual concurrently with the sensor arrangement obtaining the sensor data; and wherein the processing unit is configured to:

update the movement tracker model on the in the data storage unit based on the processed movement tracker model data, wherein the updated movement tracker model identifies the second exercise activity based on the sensor data.

* * * * *